(12) United States Patent
Zhou et al.

(10) Patent No.: US 10,392,591 B2
(45) Date of Patent: Aug. 27, 2019

(54) NUCLEIC ACID DETECTION PLATE AND DETECTION SYSTEM COMBINED WITH PIEZOELECTRIC SENSING AND LOOP-MEDIATED ISOTHERMAL AMPLIFICATION

(71) Applicant: SUZHOU CASENS CO., LTD, Suzhou (CN)

(72) Inventors: Lianqun Zhou, Suzhou (CN); Chuanyu Li, Suzhou (CN); Jia Yao, Suzhou (CN); Wei Zhang, Suzhou (CN); Zhen Guo, Suzhou (CN)

(73) Assignee: SUZHOU CORE SENSE NSC MEDICAL TECHNOLOGY CO., LTD, Suzhou (CN)

( * ) Notice: Subject to any disclaimer, the term of this patent is extended or adjusted under 35 U.S.C. 154(b) by 62 days.

(21) Appl. No.: 15/505,026

(22) PCT Filed: Nov. 2, 2015

(86) PCT No.: PCT/CN2015/093556
§ 371 (c)(1),
(2) Date: Feb. 17, 2017

(87) PCT Pub. No.: WO2016/070761
PCT Pub. Date: May 12, 2016

(65) Prior Publication Data
US 2017/0275578 A1 Sep. 28, 2017

(30) Foreign Application Priority Data
Nov. 5, 2014 (CN) .......................... 2014 1 0619272

(51) Int. Cl.
*G01N 29/24* (2006.01)
*C12M 1/34* (2006.01)
(Continued)

(52) U.S. Cl.
CPC ......... *C12M 1/3407* (2013.01); *B01L 3/5025* (2013.01); *B01L 7/00* (2013.01);
(Continued)

(58) Field of Classification Search
None
See application file for complete search history.

(56) References Cited

PUBLICATIONS

Machine Translation of CN103454439A provided by ProQuest Dialog, original document published Dec. 18, 2013.*

* cited by examiner

*Primary Examiner* — Robert T. Crow
(74) *Attorney, Agent, or Firm* — CBM Patent Consulting, LLC

(57) ABSTRACT

A nucleic acid detection plate comprises a piezoelectric sensor and at least a pipe flowing through the surface of the piezoelectric sensor, two valves intervally installed on the pipe relative to the upstream end of the piezoelectric sensor, the nucleic acid to be detected is blocked in the pipe between the two valves for isothermal amplification; the nucleic acid detection system comprises the nucleic acid detection plate described above, a thermostat capable of accommodating the nucleic acid detection plate; and a signal processor capable of being date connected to the piezoelectric sensor. The inventive method simplifies device structure in through coordinated detection by combination of thermostatic amplification and piezoelectric sensing, and improves detection efficiency.

9 Claims, 3 Drawing Sheets

(51) Int. Cl.
*B01L 7/00* (2006.01)
*C12Q 1/6806* (2018.01)
*C12Q 1/682* (2018.01)
*C12Q 1/6825* (2018.01)
*C12Q 1/686* (2018.01)
*B01L 3/00* (2006.01)
*G01N 29/22* (2006.01)

(52) U.S. Cl.
CPC ............... *B01L 7/52* (2013.01); *C12Q 1/682* (2013.01); *C12Q 1/6806* (2013.01); *C12Q 1/686* (2013.01); *C12Q 1/6825* (2013.01); *G01N 29/222* (2013.01); *G01N 29/2437* (2013.01); *B01L 2300/087* (2013.01); *B01L 2300/0838* (2013.01); *B01L 2400/0487* (2013.01); *B01L 2400/0622* (2013.01); *B01L 2400/0633* (2013.01); *G01N 2291/0255* (2013.01); *G01N 2291/0256* (2013.01); *G01N 2291/0427* (2013.01)

NUCLEIC ACID DETECTION PLATE AND DETECTION SYSTEM COMBINED WITH PIEZOELECTRIC SENSING AND LOOP-MEDIATED ISOTHERMAL AMPLIFICATION

This application is the U.S. national phase of International Application No. PCT/CN2015/093556 Filed on 2 Nov. 2015 which designated the U.S. and claims priority to Chinese Application Nos. CN 201410619272.X filed on 5 Nov. 2014, the entire contents of each of which are hereby incorporated by reference.

TECHNICAL FIELD

The present invention relates to a nucleic acid detection device, in particular to nucleic acid detection plate and detection system combined with piezoelectric sensing and loop-mediated isothermal amplification for blood detection.

BACKGROUND

Prevention and control of blood transfusion-related infectious diseases has become the focus of the whole society, the introduction of new technologies for further improving blood safety is an important part. In the field of blood transfusion, blood transfusions inevitably present a certain degree of risk as some pathogens may be present in donated blood and blood components that can cause serious clinical consequences for recipients through blood transfusion. And a wide range of related pathogens, including viruses, bacteria, parasites and a protein. The risk of transmission of bacteria through blood transfusion is still high, such as the risk of bacterial contamination is higher 250 times than virus contamination of platelet products. Some countries in Europe since 1990 started bacterial detection on all platelet products, in 2004, the United States listed bacterial detection of platelet products as a indispensable examination items.

Bacterial cultivation method is currently recognized as the most accurate method of blood bacterial detection, blood service agencies are widely used in Europe, the United States, Canada and other countries. Such as BACT/ALERT system determines the concentration of bacteria by continuing to detect the concentration of carbon dioxide in the flask, the product should be stored for 24 hours before detection, so that bacteria reaches a certain number, while cultivation also take some time to achieve positive results, usually more than 72 h. PALL EBDS detects bacterial contamination by continuously measuring oxygen consumption in the sample bag. Bacteria also need to be incubated for 24 hours. Therefore, the bacterial cultivation method is time-consuming, corresponding system configuration and maintenance costs are very high, meanwhile, because of bacterial growth with hysteresis, the bacterial cultivation method is prone to false negative results.

Rapid detection method avoids the long time-consuming defect of bacterial cultivation method, such as Scansystem, using monoclonal antibody platelet filtration, marking bacterial DNA left in the sample using a transparent agent and fluorescent, determining pollution situation through laser scanning, positive report detection time shortens to 90 minutes, But its sensitivity is only $10^3$ CFU/mL. Meanwhile, the system needs to distinguish the fluorescence signal, so it has high demand for the operator, and is difficult to promote it. At present, it is necessary to develop platelet bacterial detection equipment with high sensitivity, low cost, high-throughput to meet the blood screening and clinical diagnosis for the need of blood transfusion safety, reduce blood bacterial contamination rate, and ensure blood transfusion safety.

In the nucleic acid amplification, traditional PCR method is mostly used at present, but shortcomings of this method are low specificity, low sensitivity, slow detection speed, complex technical operation, and high requirements of the equipment, and is difficult to meet rapid diagnosis demand for grass-roots unit.

DESCRIPTION

In view of drawbacks of the prior art, A purpose of the present invention is to provide a nucleic acid detection plate and a detection system which are capable of organically combining advantages of piezoelectric sensing and loop-mediated isothermal amplification (hereinafter referred to as isothermal amplification), improving sensitivity and speed of nucleic acid detection, and reducing operation difficulty and detection costs of nucleic acid detection.

However, the nucleic acid is very easy to be contaminated, it is best able to be arranged in the closed environment for the detection, but this has led to its long detection time, high cost, and cumbersome operation steps, and high operator's request, it is difficult to obtain a generalized application. Therefore, another purpose of the present invention is to provide it is another object of the present invention to provide a novel hardware structure for nucleic acid detection which enables one-stop rapid detection of nucleic acid detection in a completely closed environment without interruption, Non contact of nucleic acid with the outside world.

For achieving the above purpose, the present invention is realized through the following technical solution:

a nucleic acid detection plate comprising: a piezoelectric sensor and at least a pipe flowing through the surface of the piezoelectric sensor, nucleic acid to be detected is introduced into the pipe in the form of liquid and flows through the surface of the piezoelectric sensor;

two valves are intervally installed on the pipe relative to the upstream end of the piezoelectric sensor, the nucleic acid to be detected is blocked in the pipe between the two valves before flowing through the piezoelectric sensor for loop-mediated isothermal amplification in order to be sensed by the piezoelectric sensor.

Preferably, Wherein the two valves are respectively a first valve close to the piezoelectric sensor and a second valve remote from the piezoelectric sensor, wherein the upstream end of the second valve is further provided with a three-way valve, one port of the three-way valve is connected with a sample cell for storing the nucleic acid to be detected, auxiliaries necessary for nucleic acid amplification, and additives for helping the nucleic acid to be sensed by the piezoelectric sensor after amplifying, and the other port of the three-way valves is connected with the outside of the nucleic acid detection plate for introducing cleaning solution or buffer solution into the pipe.

Preferably, the pipe relative to the downstream end of the piezoelectric sensor is connected with a waste liquid pool for recovering the nucleic acid to be detected which is sensed through flowing through the piezoelectric sensor to avoid contamination.

A nucleic acid detection system comprises the nucleic acid detection plate described above, a thermostat capable of accommodating the nucleic acid detection plate; and a signal processor capable of being date connected to the piezoelectric sensor.

Preferably, the nucleic acid detection system also comprises an injection pump for driving liquid to flow within the pipe.

Preferably, the first valve, the second valve, and the three-way valve are all electrically controlled valves; and a lifting platform is arranged above the nucleic acid detection plate, and a telescopic first probe is provided at the position of the lifting platform opposite to the first valve, the second valve and the three-way valve for selectively opening and closing of on trigger electronically controlled valve.

Preferably, a telescopic second probe is provided at the position of the lifting platform opposite to the piezoelectric sensor to selectively control the data connection between the piezoelectric sensor and the signal processor.

Preferably, an inlet is arranged on the position of the thermostat opposite to the upper part of the sample cell.

Preferably, the inlet is filled with a seal.

Preferably, the surface of the thermostat is also provided with a threading hole for through-tube wiring, and the threading hole is filled with a seal.

The advantages of the present invention are as follows.

1. The inventive device simplifies device structure through coordinated detection by combination of thermostatic amplification and piezoelectric sensing, and improves detection efficiency through high specificity of the piezoelectric sensor, the detection limit is 0.1 pg/mL;

2. The whole closed structure can avoid the problem of aerosol contamination which may be involved in the nucleic acid detection, and is easy to realize mass production, the detection system is suitable for solving the problems caused by existing blood pathogen especially platelet bacterial contamination of long detection time, low flux, high cost, cumbersome steps and other issues.

DETAILED DESCRIPTION

Figure 1:
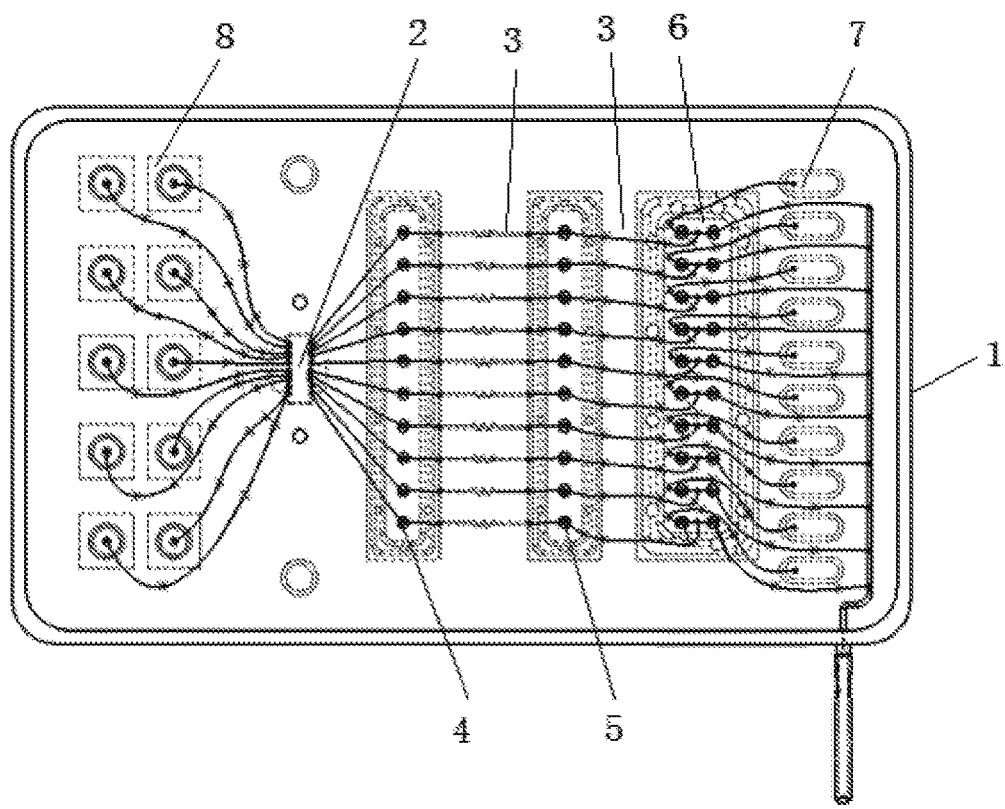
FIG. 1 is the structure diagram of the nucleic acid detection plate.
Figure 2:
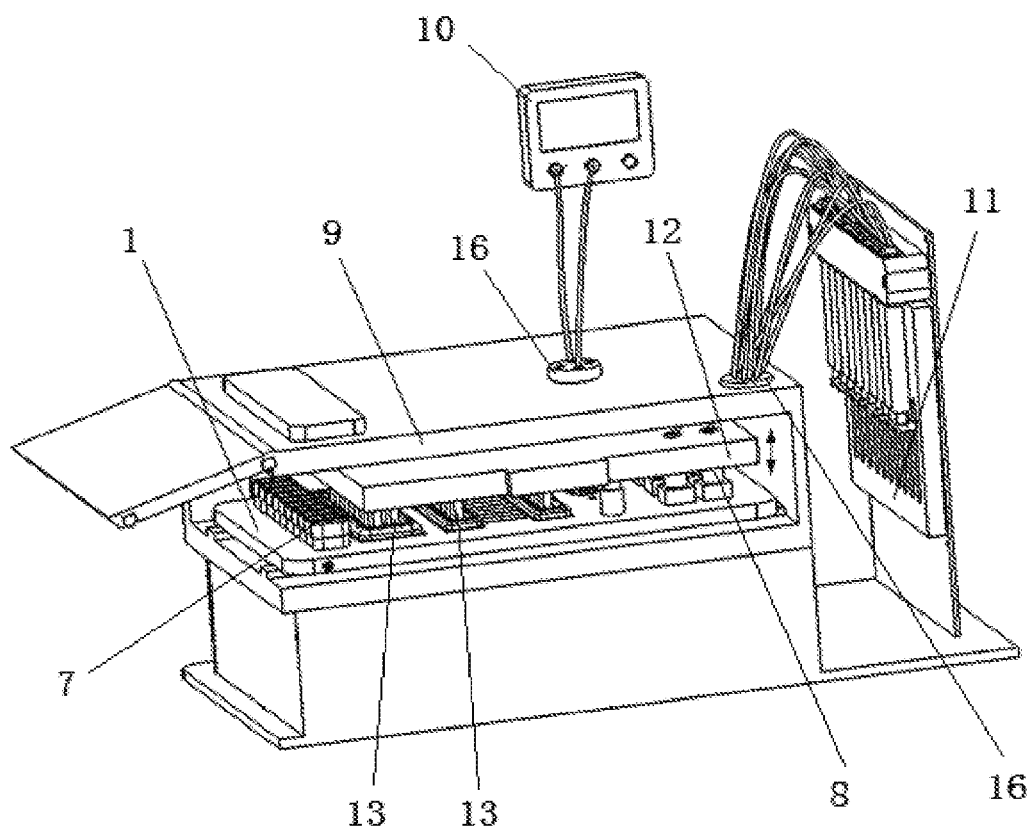
FIG. 2 is the structure diagram of the nucleic acid detection system.
Figure 3:
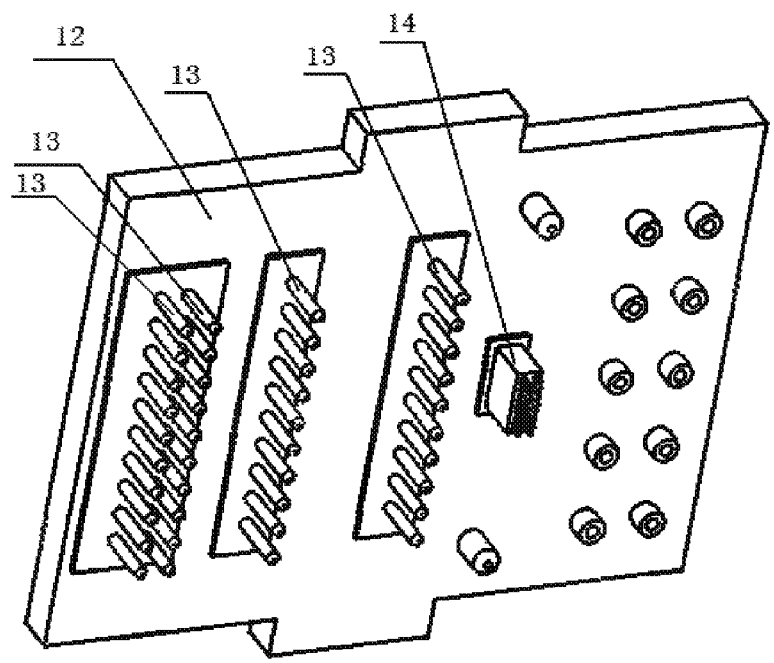
FIG. 3 is the structure diagram of the lifting platform in the nucleic acid detection system.
Figure 4:
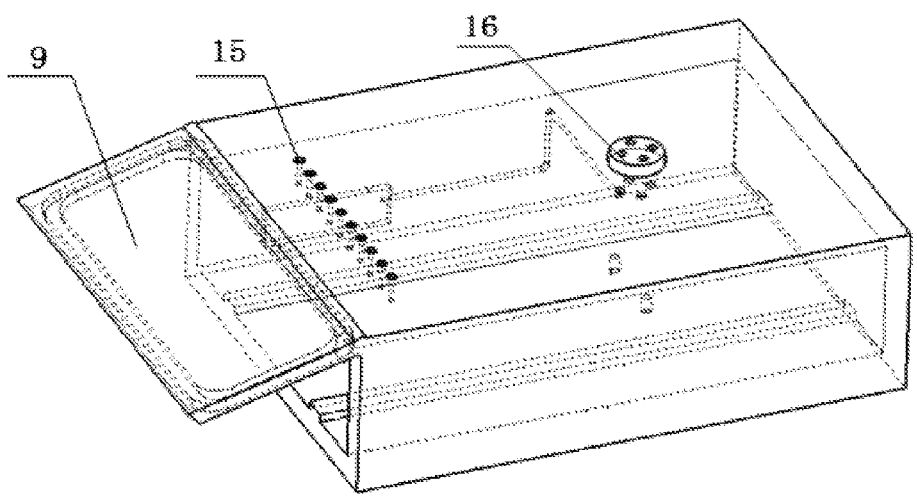
FIG. 4 is the structure diagram of the thermostat in the nucleic acid detection system.

The present invention will now be described in further detail with reference to the accompanying drawings as required:

As shown in FIG. 1 to FIG. 4, The present invention provides an embodiment of a nucleic acid detection plate 1 comprising a piezoelectric sensor 2 and at least a pipe 3 flowing through the surface of the piezoelectric sensor, wherein, pipe 3 may be a plurality of pipes, each of which is independent from one another in order to simultaneously detect multiple samples, nucleic acid to be detected is introduced into the pipe 3 in the form of liquid and flowing through the surface of the piezoelectric sensor 2. The specific form of the nucleic acid to be detected flowing through the surface of the piezoelectric sensor 2 may not be limited, It is only necessary to ensure that the nucleic acid to be detected can contact with the sensing surface of the piezoelectric sensor 2. When pipe 3 contains a plurality of pipes, corresponding surfaces of the piezoelectric sensor 2 should be provided with the same number of sensing faces independent of each other to meet the multi-channel detection requirements. The piezoelectric sensor 2 is preferably a piezoelectric acoustic wave sensor, and more preferably a Lamb wave sensor.

Two valves are intervally installed on the pipe 3 relative to the upstream end of the piezoelectric sensor 2. The nucleic acid to be detected is blocked in the pipe between the two valves before flowing through the piezoelectric sensor 2 for isothermal amplification in order to be sensed by the piezoelectric sensor 2, The purpose of isothermal amplification is to increase the size of the nucleic acid molecule so that it can be more easily adsorbed and sensed by the piezoelectric sensor 2. As long as the distance between the two valves is fixed, then the volume of this pipe can be calculated, thus the concentration of nucleic acid to be detected can be convenient for conversion.

In the above embodiment, the two valves are a first valve 4 close to the piezoelectric sensor 2 and a second valve 5 remote from the piezoelectric sensor 2, respectively, and the upstream end of the second valve 5 is also provided with a three-way valve 6, And one port of the three-way valve 6 is connected with a sample cell 7 for storing the nucleic acid to be detected, auxiliaries necessary for nucleic acid amplification, and additives for helping the nucleic acid to be sensed by the piezoelectric sensor after amplifying, the additives for helping the nucleic acid to be sensed by the piezoelectric sensor after amplifying is usually antibody molecules modified the surface of the piezoelectric sensor; modified piezoelectric sensor surface can adsorb the nucleic acid molecules to be detected, of course, the specific kind of modifying molecule depends on the specific kind of the nucleic acid to be detected. The auxiliaries necessary for nucleic acid amplification and the additives for helping the nucleic acid to be sensed by the piezoelectric sensor after amplifying will not react when two coexist, both before the nucleic acid to be detected is stored in the sample pool, when the nucleic acid to be detected is injected into the sample cell, the three start to be driven into the pipe between the first valve 4 and the second valve 5 for amplification, and since the amplification rate is not fast, the three coexist for a short time do not affect amplification results. The other port of the three-way valve 6 is connected to the outside of the nucleic acid detection plate 1 for introducing cleaning solution or buffer solution into the pipe. The function of the three-way valve 6 is to control the inflow of the liquid in the sample cell 7 and buffer solution or cleaning solution, respectively, to improve the automation degree of the detection and detection efficiency.

In the above embodiment, the pipe 3 relative to the downstream end of the piezoelectric sensor is connected with a waste liquid pool 8, the waste liquid pool 8 is used for recovering the nucleic acid to be sensed by the piezoelectric sensor 2 to avoid contamination.

The present invention provides an embodiment of a nucleic acid detection system comprising a nucleic acid detection plate 1 as described above, a thermostat 9 capable of accommodating the nucleic acid detection plate 1; and a signal processor 10 capable of being date connected to the piezoelectric sensor 2.

In this embodiment, the nucleic acid detection system also comprises an injection pump 11 for driving liquid to flow within the pipe, the injection pump 11 can be connected to the top of the waste liquid pool 8.

In this embodiment, the first valve 4, the second valve 5, and the three-way valve 6 are all electrically controlled valves; and a lifting platform 12 is arranged above the nucleic acid detection plate 1, and a telescopic first probe 13 is provided at the position of the lifting platform 12 opposite to the first valve 4, the second valve 5 and the three-way valve 6 for selectively opening and closing of on trigger electronically controlled valve. This control can be controlled by an integrated control chip. The control mode of the probe can be set freely, can choose to set when probing probe contact with the probe, the valve is opened, and vice versa; can also choose to set when probing probe touch the probe, the valve is closed, and vice versa. In addition, the control of the lifting platform can also be selected of chip motor control, mechanical semi-automatic control or pure manual control according to actual needs.

In this embodiment, a telescopic second probe 14 is provided at the position of the lifting platform 12 opposite to the piezoelectric sensor 2 to selectively control the data connection between the piezoelectric sensor 2 and the signal processor 10. After the probe touches the electrode of the two ends of the piezoelectric sensor, the piezoelectric crystal has a reverse piezoelectric effect, so that the vibration occurs of the film of the piezoelectric sensor 2, and then mechanical energy is transformed into electrical energy through the positive piezoelectric effect, resulting in output power signal. The vibration frequency is changed according to quality change of the surface of the sensor, so as to calculate the content of the nucleic acid to be detected.

In this embodiment, an inlet 15 is arranged on the position of the thermostat 9 opposite to the upper part of the sample cell 7, the inlet 15 serves to facilitate injection.

In this embodiment, the inlet is filled with a seal. The specific form or type of the seal is not limited, it is mainly used to ensure constant temperature effect of the thermostat, in order to ensure amplification efficiency in line with the expected result.

In this embodiment, the surface of the thermostat 9 is also provided with a threading hole 16 for through-tube wiring, and the threading hole 16 is filled with a seal. The specific form or type of the seal is not limited.

The working process of nucleic acid detection system is:

1) opening the side plate of the thermostat 9, placing the nucleic acid detection plate 1 in the thermostat 9, closing the side plate, opening the thermostat 9 to increase the temperature to the required temperature for amplification;

2) opening all valve, closing the port of the three-way valve connected to the sample cell 7, introducing buffer solution through injection pump 11 driving into the pipe 3 for cleaning;

3) closing the port of the three-way valve connected to buffer solution, opening the port of the three-way valve connected to the sample cell 7, keeping conducting state of the first valve 4 and the second valve 5; injecting the nucleic acid to be detected from the inlet 15 into the sample cell 7 (auxiliaries may be previously injected into the sample cell 7);

4) pumping sample to be detected by the injection pump 11 into the pipe between the first valve 4 and the second valve 5, closing all the valves, and performing isothermal amplification of the nucleic acid to be detected;

5) after completion of the amplification, opening the first valve 4, the second valve 5 and the port of the three-way valve connected with buffer solution, introducing buffer solution; at the moment, nucleic acid to be detected is passed through the piezoelectric sensor 2 and nucleic acid to be detected through modifying molecules of auxiliaries is adsorbed into the surface of the sensor causing quality changes, thus the vibrational frequency of the sensor is changed, the signal processor 10 acquires phase and amplitude variations of the piezoelectric sensor 2, recording and storing;

6) pumping all samples to the waste liquid pool 8, cleaning the surface of the sensor by buffer solution; detection is completed, discarding the nucleic acid detection plate 1, exchanging a new nucleic acid detection plate 1 to start the next round of detection. The figure shows 10 channels of detection, that is, one time single detection plate can detect 10 samples at the same time.

Although the embodiments of the present invention have been disclosed above, they are not limited to the applications previously mentioned in the specification and embodiments, and can be applied in various fields suitable for the present invention. For ordinary skilled person in the field, other various changed model, formula and parameter may be easily achieved without creative work according to instruction of the present invention, changed, modified and replaced embodiments without departing the general concept defined by the claims and their equivalent are still included in the present invention. The present invention is not limited to particular details and illustrations shown and described herein.

What is claimed is:

1. A nucleic acid detection system comprising a nucleic acid detection plate, liquid test nucleic acids and a signal processor, wherein the nucleic acid detection plate comprises a piezoelectric sensor and at least a tube with a sidewall that goes through the surface of the piezoelectric sensor, the liquid test nucleic acids flowing through the inside of the tube;

two valves, a first valve and a second valve, are installed in the inside of the tube, the test nucleic acids being capable of being detained in the tube between the two valves before flowing through the piezoelectric sensor for loop-mediated isothermal amplification in order to be sensed by the piezoelectric sensor; and the signal processor connects to the piezoelectric sensor.

2. The nucleic acid detection system according to claim 1, wherein the piezoelectric sensor is installed between the first valve and the second valve; the test nucleic acids flowing through the first valve, the piezoelectric sensor and the second valve, wherein a three-way valve is provided on the tube between the first valve and the second valve, one port of the three-way valve is connected with a sample cell for storing the test nucleic acids, auxiliaries for nucleic acid amplification, and additives for helping the nucleic acid to be sensed by the piezoelectric sensor after amplifying, and the other port of the three-way valve is connected with the outside of the nucleic acid detection plate for introducing cleaning solution or buffer solution into the tube.

3. The nucleic acid detection system according to claim 2, being characterized in that: the tube relative to the downstream end of the piezoelectric sensor is connected with a waste liquid pool for collecting the test nucleic acid flowing through the piezoelectric sensor to avoid contamination.

4. The nucleic acid detection system according to claim 1, wherein a thermostat connects to the nucleic acid detection plate.

5. The nucleic acid detection system according to claim 1, wherein an injection pump is installed for driving liquid to flow within the tube.

6. The nucleic acid detection system according to claim 4, being characterized in that: the first valve, the second valve, and the three-way valve are all electrically controlled valves; and a lifting platform is arranged above the nucleic acid detection plate, and a telescopic first probe is provided at the position of the lifting platform opposite to the first valve, the second valve and the three-way valve for selectively opening and closing by an electronically controlled valve.

7. The nucleic acid detection system according to claim 6, being characterized in that: a telescopic second probe is provided at the position of the lifting platform opposite to the piezoelectric sensor to selectively control the data connection between the piezoelectric sensor and the signal processor.

8. The nucleic acid detection system according to claim 4, being characterized in that: an inlet is arranged on the position of the thermostat opposite to the upper part of the sample cell.

9. The nucleic acid detection system according to claim 4, being characterized in that: the surface of the thermostat is also provided with a threading hole for through-tube wiring, and the threading hole capable of being sealable.

\* \* \* \* \*